United States Patent [19]
Zelniker et al.

[11] Patent Number: 5,444,218
[45] Date of Patent: Aug. 22, 1995

[54] ELECTRICALLY HEATED PRESSURE PROCESSOR APPARATUS FOR PRODUCTION OF DENTAL PROSTHESES

[76] Inventors: Lilian Z. Zelniker; Alberto Sternberg, both of A.V. Garibaldi 1969/603, Montevideo, CP 11800, Uruguay

[21] Appl. No.: 960,860

[22] Filed: Oct. 14, 1992

[30] Foreign Application Priority Data

Oct. 23, 1991 [UY] Uruguay .................. U-2974 U
Oct. 23, 1991 [UY] Uruguay .................. 23305

[51] Int. Cl.⁶ .................................... F27D 7/02
[52] U.S. Cl. .................................. 219/440; 219/431
[58] Field of Search ............. 219/440, 431; 99/408; 433/25, 32

[56] References Cited

U.S. PATENT DOCUMENTS

| | | | |
|---|---|---|---|
| 1,440,826 | 1/1923 | Hager | 219/431 |
| 2,691,090 | 10/1954 | Vischer | 219/431 |
| 2,973,481 | 8/1961 | Mies | 99/408 |
| 2,984,171 | 5/1961 | Lee | 219/431 |
| 3,194,662 | 7/1965 | Nelson | 219/431 X |
| 3,604,895 | 9/1971 | MacKay | 219/440 |
| 3,609,296 | 9/1971 | Blair | 219/440 |
| 4,362,148 | 12/1982 | Luebke | 219/440 |
| 4,771,162 | 9/1988 | Schatz et al. | 219/440 X |

*Primary Examiner*—Teresa J. Walberg
*Attorney, Agent, or Firm*—Fisher, Christen & Sabol

[57] ABSTRACT

In the present invention dental prostheses are cured without the use of dental flasks using an electrically heated pressure vessel. The dental prosthesis is cured while in a plaster chamber which is placed in a curing container with ambient water. The apparatus includes a perforated table for supporting the curing container during heat curing. The vessel has a lid for sealing the top, an inlet for injection of compressed air, an outlet for exhausting of compressed air, and an electrical resistance heating means for heating water held in the vessel. The curing container holds ambient temperature water at a level which covers the plaster chamber prior to submerging the curing container in the vessel containing water at a temperature of 90° C. to 100° C. The table supports the outing container in the vessel so that the top edge of the curing container is above the level of water held by the vessel. The present invention provides that the plaster chambers with the dental prosthesis inside of it being already aggregated heat curing acrylic, are those which maintain the vertical dimension. They are within the curing container while they are gradually heated by the hot water of the processor. Pressure which could fracture the model and the prosthesis is avoided.

16 Claims, 5 Drawing Sheets

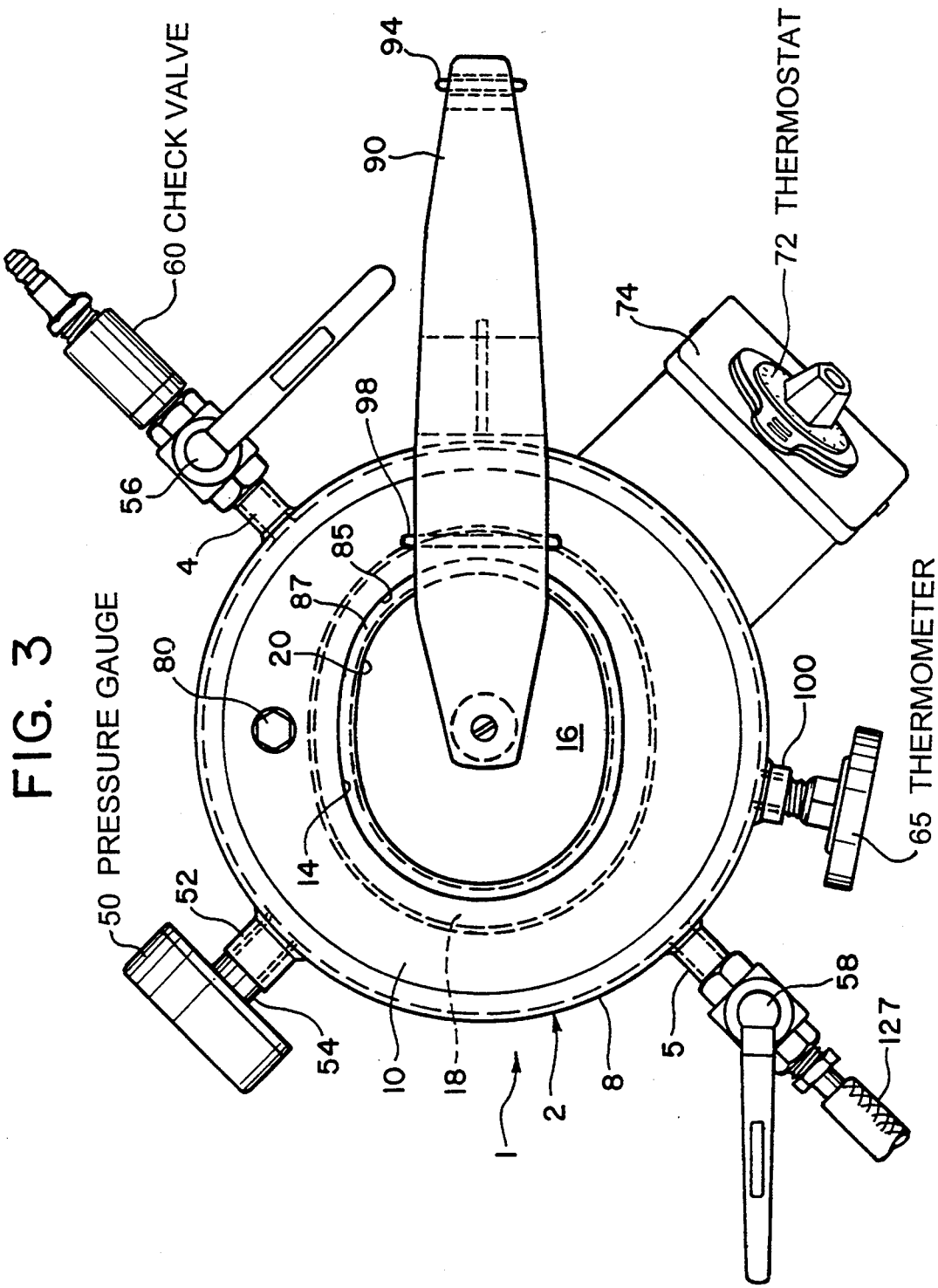

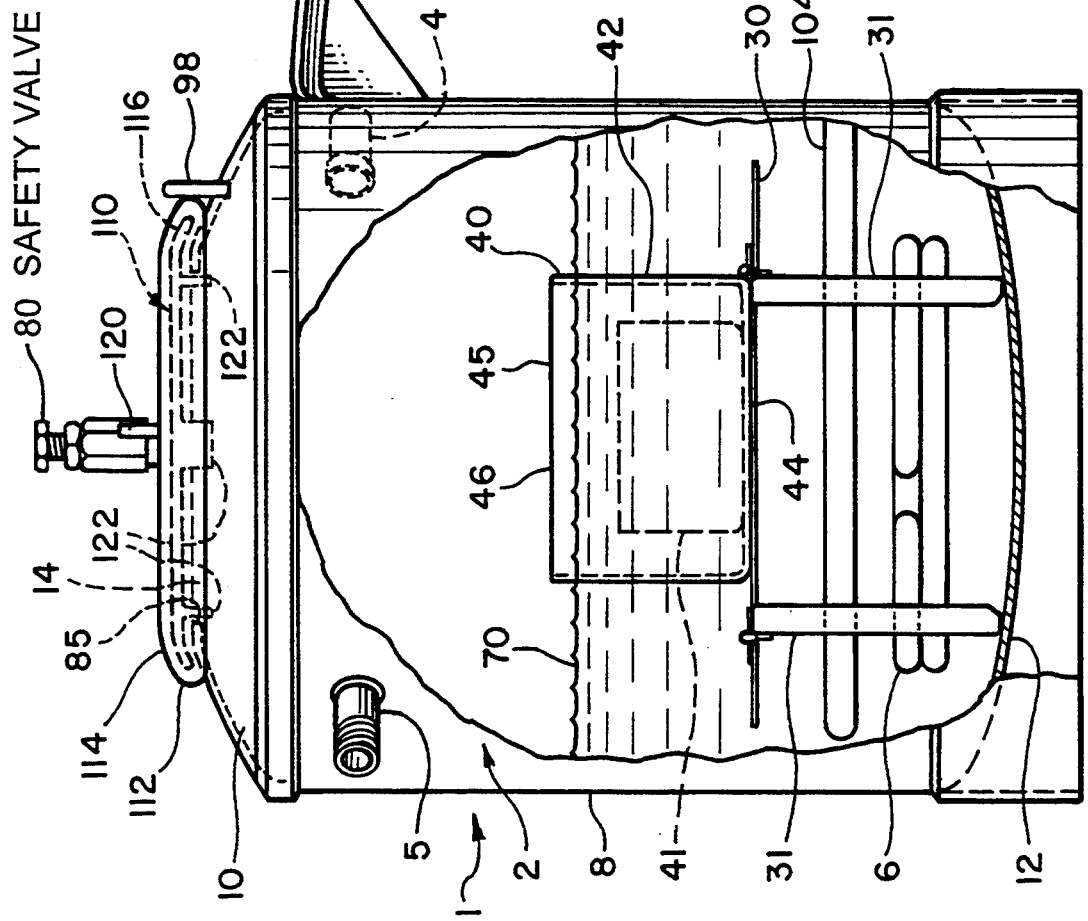
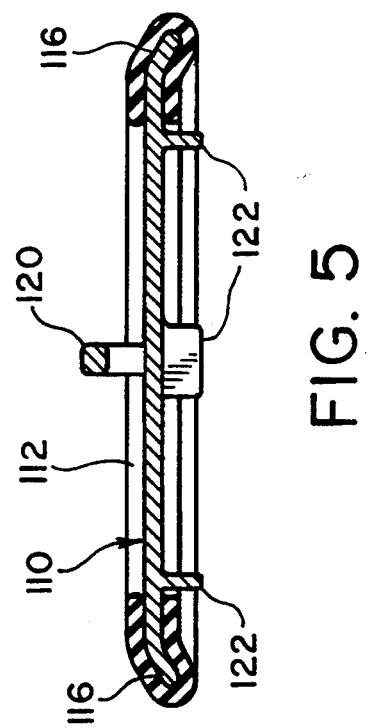

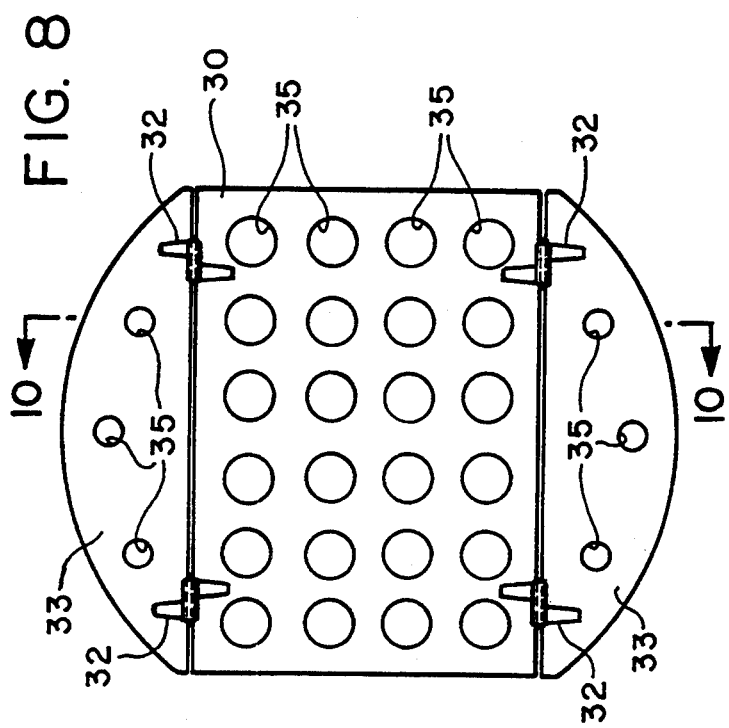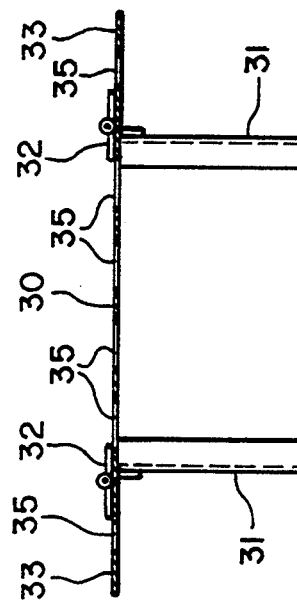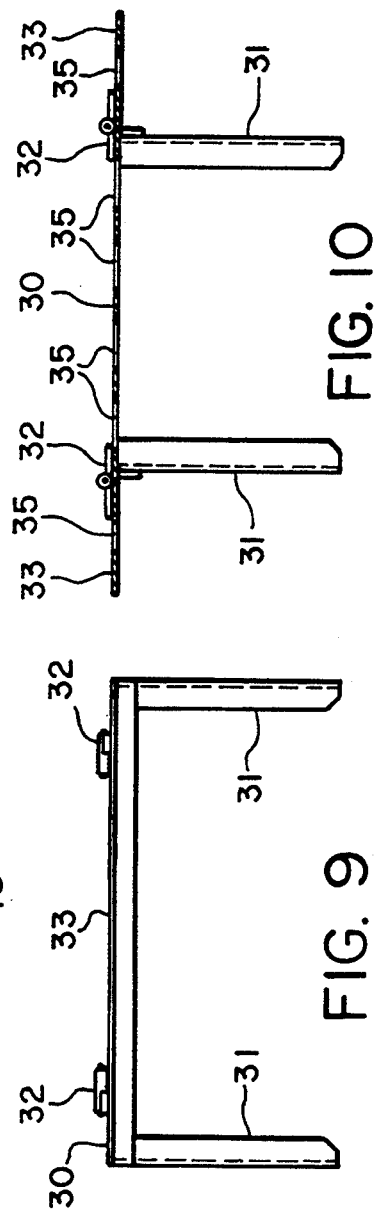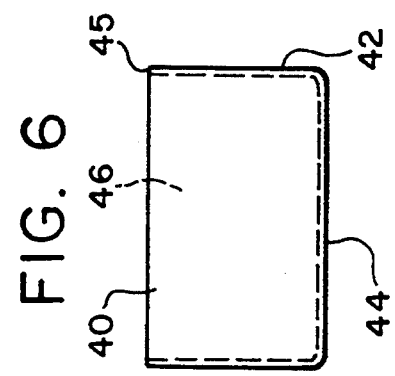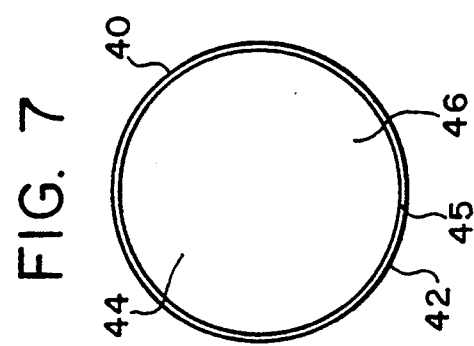

ELECTRICALLY HEATED PRESSURE PROCESSOR APPARATUS FOR PRODUCTION OF DENTAL PROSTHESES

FIELD OF THE INVENTION

The present invention provides a process and apparatus for the production of dental prostheses without the use of dental flasks.

BACKGROUND OF THE INVENTION

In the production of dental prosthetics using a dental flask, methyl methacrylate is generally pressed in the flask to adapt it to the form of a model. During the pressing stage and the opening stage of the flask process fracturing of plastic or porcelain teeth, cobalt chromium clasps, and the model frequently occurs. In addition, the flask process is time-consuming and requires considerable physical strength for pressing of the flask in a vise. The flask process often results in a change in the vertical dimension of the dental prosthetic when pressing is performed which adversely affects its fit in the toothless mouth.

The present invention provides an electrically heated pressure processor apparatus for producing dental prostheses without the use of dental flasks. The dental prostheses may be produced in almost less than half of the time, using less material and without the physical exertion needed for pressing dental flasks. The dental prostheses are made with fluid heat curing acrylic added in a plaster chamber which is vibrated to adapt to the positive model of the plaster chamber. The plaster chamber is placed in the apparatus of the present invention for heat curing and avoiding variations in vertical dimension. In addition, they adapt well to the toothless mucous and present a very smooth surface that facilitates polishing and avoids the formation of microbial plaques, parodontium illness, and alimentary retention.

SUMMARY OF THE INVENTION

The present invention provides an apparatus and procedure for the finishing of dental prostheses which totally eliminates the use of dental flasks. The apparatus and procedure accelerates the completion of complete dentures, such as overdentures, opturating dentures, and transparent palate dentures, partial dentures, orthodontic appliances, occlusal plates for the relaxation of muscles (mio-relaxing splint plates), rebasing, and repairs.

The apparatus for heat curing of an acrylic dental prosthesis while the prosthesis is in a plaster chamber comprises a vessel for boiling or heating water, a resistance heating means for heating water held in the vessel, means for supplying compressed air to the vessel, one or more curing containers, and a foldable, perforated table for supporting the curing containers in the vessel. The curing container is filled with water to a level which covers the plaster chamber after submerging the container in the vessel. The table supports the curing container in the vessel so that the top edge of the curing container is above the level of water held by and heated by the heating means in the vessel. This arrangement permits: 1) heating of the water in the vessel to a temperature sufficient for heat curing of the acrylic dental prosthesis, and 2) then placement of the outing container with the water covered, prosthesis-containing plaster chamber into the heated water to heat the water in the outing container without subjecting the dental prosthesis to burning. The resistance heating means is located below the table which supports the curing container. The use of a perforated table permits the circulation of the heated water around the curing container.

The plaster chambers of rock plaster which contain the heat-curing acrylic dental prosthesis may be a complete plaster chamber, semi-plaster chamber, or special plaster chamber. The plaster chambers are made using a rock plaster to make a base model (positive) of a toothless jaw, inserting teeth, covering the model and teeth with wax, forming plaster fronts, and covering the prosthesis. The plaster chamber with the waxing is subjected to a cold temperature, moistening process at ambient temperature (20° C. to 25° C.) in the processor of the present invention. The wax is eliminated using hot water and soda. The plaster chamber, with the heat curing acrylic already aggregated inside it is varnished and dried at ambient temperature. The inlets of the plaster chamber are covered with plaster of paris and then the plaster chamber is placed in the curing container with ambient temperature water for heat curing of the acrylic in the apparatus of the present invention. The moistening or cold process and the heat curing process are conducted in the processor at a pressure of 3.5 bars or 50 psi. The cold process is conducted at 20° C. to 25° C. (ambient temperature) for three minutes. The heat curing process is conducted at 90° C. to 100° C. for a cooking time of 20 to 25 minutes.

BRIEF DESCRIPTION OF THE DRAWINGS

FIG. 3 is a top view of the apparatus of FIG. 1.

FIG. 4 is a front view of the apparatus of the present invention with a break-away view of the inside, and with the lid replaced by a protective lid.

FIG. 5 is a perspective view of the cross-sectional lid of FIG. 4.

FIG. 6 is a front view of a curing container for use in the present invention.

FIG. 7 is a top view of the curing container of FIG. 6.

FIG. 8 is a top view of a table for supporting the curing container in accordance with the present invention.

FIG. 9 is a front view of the table of FIG. 8.

FIG. 10 is a right side sectional view taken along line 10—10 of FIG. 8.

DETAILED DESCRIPTION OF THE INVENTION

Figure 1:
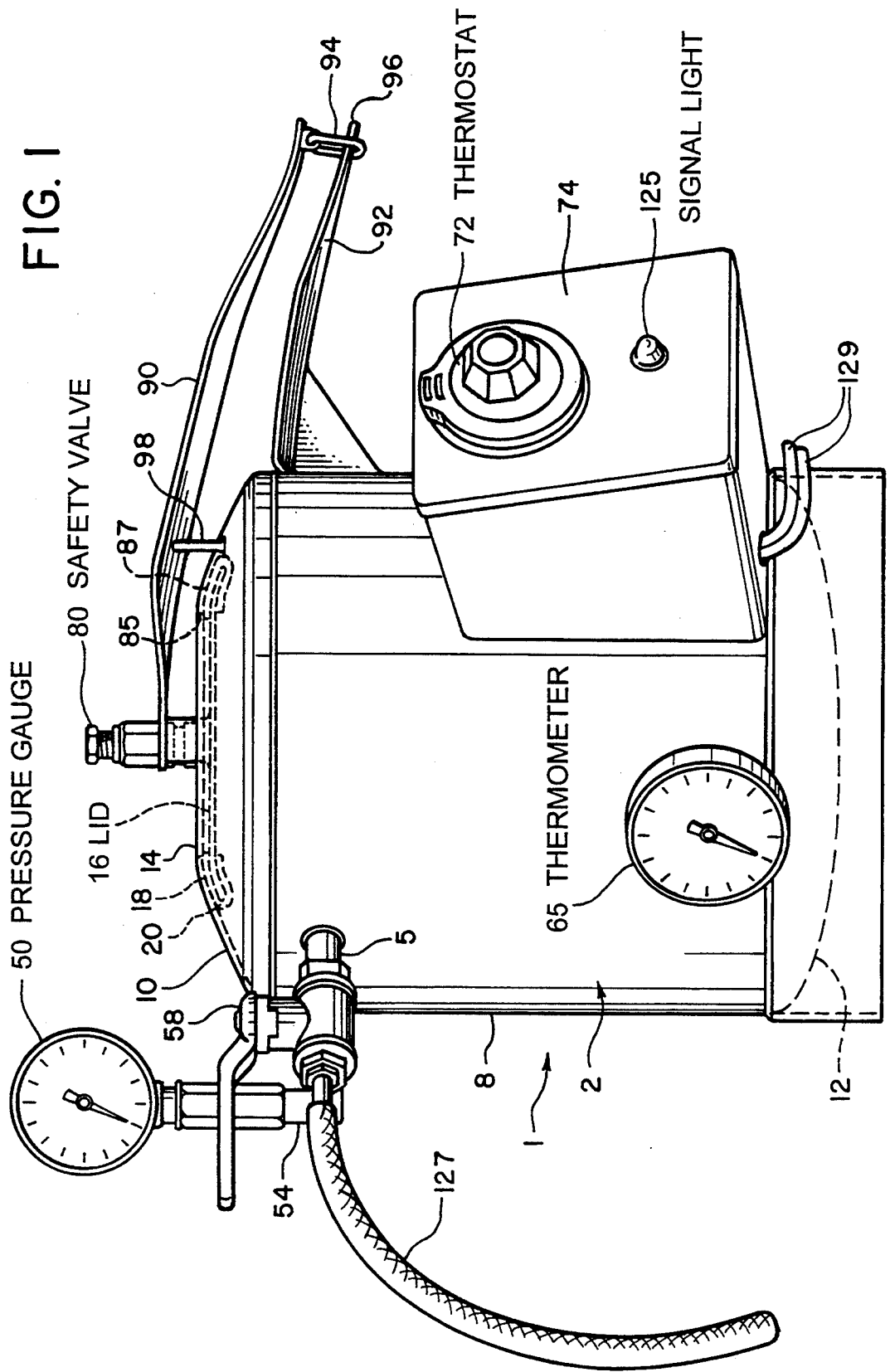
FIG. 1 is a front view of the apparatus for heat curing of acrylic dental prostheses with the lid sealed for heat curing in accordance with the present invention.
Figure 2:
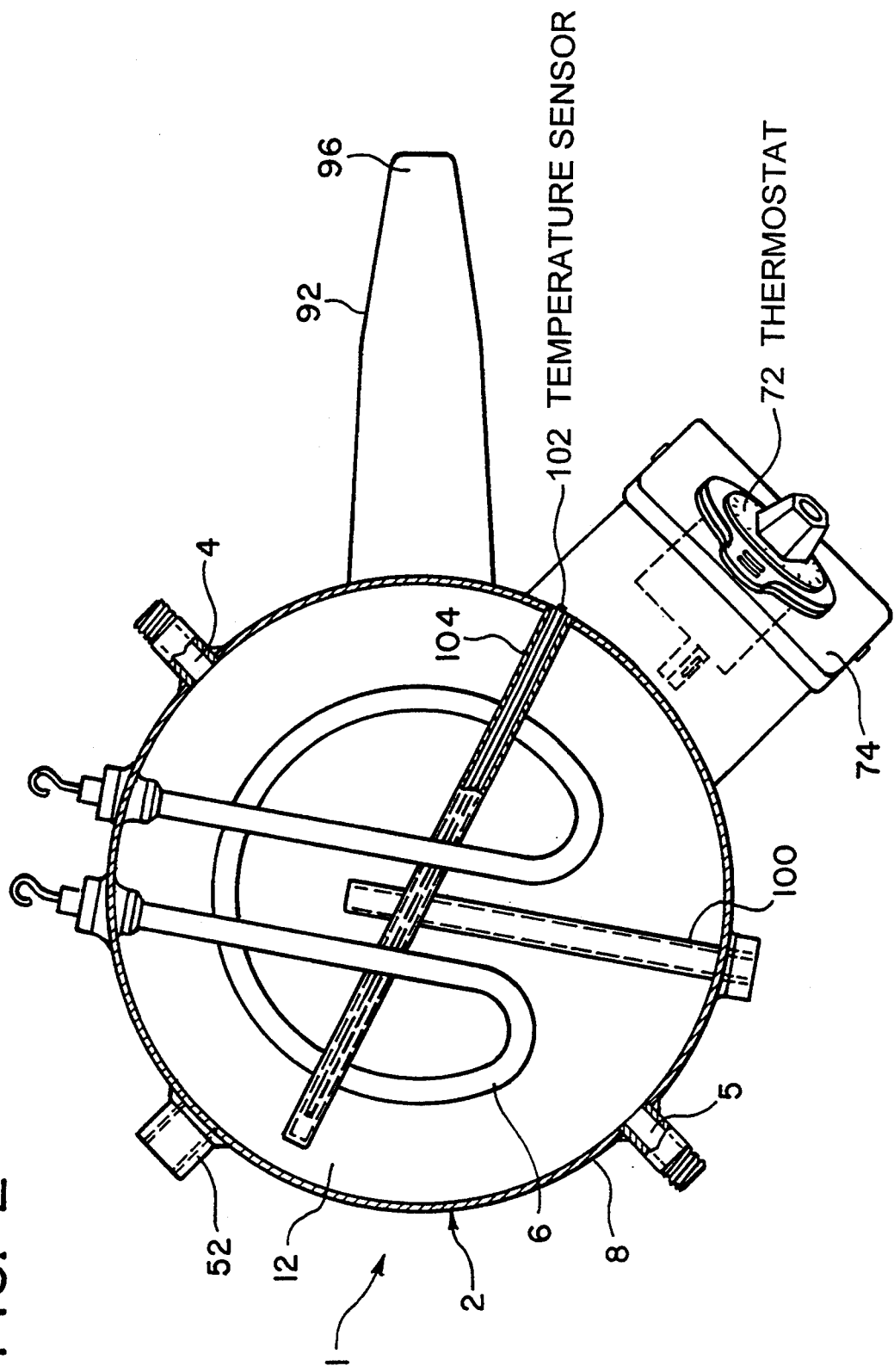
FIG. 2 is a top view of the apparatus of FIG. 1 with the top, hoses, curing container, and table removed showing the resistance heating means of the present invention.

The processor or apparatus 1 for producing dental prostheses in heat curing acrylic, as shown in FIGS. 1–4, comprises an internal cooking boiler or vessel 2 for boiling or heating water with compressed air injection via inlet 4. Caloric energy for the water is provided through an electric resistance heating means 6. This boiler or vessel 2 is made of 2 mm. thick stainless steel. It comprises a cylinder 8 which is 232 mm. in diameter and 278 mm. high. The side is cylindrical and both the top 10 and the bottom or floor 12 are concave. The top 10 has an oval opening 14 which is 132 mm. long and 105 mm. wide, in which is placed an oval lid 16 which is larger than the opening 14. The lid 16 is 160 mm.×130 mm. and its external border 18 has a 7 mm. thick ring 20 contouring it. This ring 20 is made of vulcanized, or heat molded rubber, and is used to prevent the compressed air from leaving when it is injected in the boiler 2.

The boiler 2 has an electric shielded resistance of 220 volts, and 800 watts of power, to heat the water inside the processor 1. It is used as a means of cooking the heat curing acrylic of the different prostheses which are inside.

Moreover, as shown in FIG. 4, inside there is a stainless steel table 30 having legs 31 and hinged folding portions 33. On the table 30 there may be placed three or four curing containers 40 that fit inside the processor 1 for treatment of the plaster chamber 41. The table 30 is 210 mm. in diameter and about 75 mm. high. The table 30 is perforated with perforations 35, as shown in FIGS. 8 and 10, to maintain a correct hot water circulation around the curing containers 40.

Additionally, as shown in FIGS. 8, 9 and 10, the table 30 can be folded by means of hinges 32 to enable easy removal from the inside of the processor vessel 2. The curing containers 40 are of stainless steel and, as shown in FIGS. 4, 6 and 7 has a cylindrical body 42, flat bottom 44, a top edge 45, and a top opening 46. Two curing containers are 102 mm. in diameter and 60 mm. high and another two are 85 mm. in diameter and 56 mm. high.

To measure the air pressure that is injected via inlet 4 inside the vessel 2, a pressure gauge or barometer 50 is provided in the upper portion of the side of the main cylinder 8 beside the top 10. It is joined by a welded nipple 52 and a chromium bronze elbow 54. In the processor two ball valves 56 and 58 connected to inlet 4 and outlet 5, respectively, were placed for the injection of compressed air and the exhaust of air and steam in opposite positions on the cylinder 8. A check valve 60 is connected to inlet ball valve 56 as shown in FIG. 3.

A 0° C.–150° C. thermometer 65 was also placed on the cylinder 8 to measure the temperature of the water 70 held by the vessel 2. The water temperature is controlled by a thermostat 72 placed in a vertical box 74 welded to the external wall surface of the processor boiler 2. This box 74 is 13 cm. long, 9.5 cm. wide and 7.5 cm. high. All the water 70 used by the processor boiler 2 is about 6 liters and it is used to cure the dental prostheses in heat curing acrylic, because this is the only way to harden the acrylic without burning, maintaining its homogeneous molecular structure and smooth texture.

The curing containers 40 are used to place the plaster chamber with their prostheses into the vessel 2, both for the cold process and for the heat-curing process when heat-curing acrylic is added. When a plaster chamber is placed in a curing container 40, water has to be added inside up to 1 cm. below the upper edge 45 of the container 40.

In the upper part or top 10 beside the oval opening 14, a safety valve 80 is placed in case the injected air exceeds the maximum pressure allowed for the process and prostheses. Beside any damage to them being avoided, the security of the processor itself is ensured.

The top 10 of the processor 1 has an oval lid 16 which is approximately 1 cm. larger than the oval opening 14 in all its perimeter, to adapt to the inside edge 85 of the opening 14 by forming an oval crown 87 that covers the opening 14 from the inside of the vessel 2. When properly placed with the handle 90 of the lid 16, it is adjusted on the fixed arm 92 of the processor vessel 2 with a ring 94 that fits in the narrow end part 96 of the arm 92, fastening the handle 90 over bridge 98 like a spring.

As the lid 16 a vulcanized rubber ring 20, it must be placed obliquely and across the oval opening 14 and afterwards it must be rotated 90° until the longer part of the oval lid 16 coincides with the same part of the oval opening 14. Once a close fitting has been obtained, it must be sealed using the ring 94. The vessel 2 can then be filled with compressed air until a pressure of 50 psi is obtained to carry out either moisturizing a plaster chamber in the cold process or heat-curing a prosthesis by adding heat curing acrylic.

To control temperature from the outside and verify correct working of the resistance heating means 6 and the thermostat 72 the 0° C. to 150° C. thermometer 65 is placed to extend through the cylinder wall 8. The thermometer 65 is located in a pipe 100 welded to the main wall 8 of the processor boiler 2 and is placed in the center of the resistance heating means 6 to get the best sensitivity to the temperature of the boiling water 70 inside the processor 1.

The thermostat 72 is connected to a thermostat filament 102 which is placed in a pipe 104 and welded to the processor 1 anywhere, passing through the center, but not reaching the other side, and passing over the resistance heating means 6. Both pipes 100 and 104 are made of stainless steel.

As the use of the processor 1 requires a vulcanized rubber lid 16 and temperature is raised gradually to reach working temperature, steam (water vapor) is produced, which damages the rubber 20 if the lid 16 is placed on the opening 14. For this reason, as shown in FIGS. 4 and 5, another thinner stainless steel protective lid 110 with the same shape is made. Also, a simple non-vulcanized rubber ring 112 which is fit to the edge 114 of the lid 110 is inserted into the slot 116 of the rubber ring 112.

The protection lid 110 has a small handle 120 and small legs 122 in the obvers in order to be placed correctly in the opening 14. The function of this lid 110 is only to prevent water vapor from leaving the processor 1. Also, it helps to preserve the main lid 16 which is very expensive. The protective lid 110 is also used after the curing stage of any prosthesis to maintain water temperature, as long as possible until the next work is performed.

In the external box 74 where the thermostat 72 and the light switch (not shown) are, an indicating neon light 125 has been placed. Light 125 turns off when the water 70 is at the right temperature and helps to show that the thermostat 72 is working properly. A plastic pipe 127 for the water or steam had to be added to the exhaust valve (ball valve) 58 so that the air and steam can get out together and do not burn the hands of whoever is working at the time. The pipe 127 is approximately 25 cm. long. Moreover, a bottle or container may be added to avoid spilling water on the work place. The electric energy that the resistance heating means 6 receives comes from a bipolar rubber protected power cord 129, to avoid any damage. Also, the wires of power cord 129, which carry energy to the thermostat 72, are shielded by glass fiber and are covered with a glass-fiber insulation to be isolated from the wall 8 of the processor 1.

EXAMPLE

For the cold process, or moistening step, the plaster chamber 41, either complete, semichamber or special, is placed in the curing container 40 with the waxing, and submerged in running water for introduction into the processor 1 at ambient temperature (20° to 25° C.). The temperature 65 is checked on the processor's thermometer.

The quantity of water in the processor should also be checked, and the process is as follows:

Take a curing container 40 filled with water, introduce it into the processor 1, and set it on the inside table 30 checking that water 70 reaches up to 1 cm. below the upper edge 45 of the curing container 40.

Then remove the corresponding plaster chamber 41 from the curing container submerged in running water, and introduce it into the container 40 in the processor. Close the latter with the main lid 16. Then fit the ring 94 of the lid handle 90 with the fixed arm 92 of the processor. Turn off the air outlet valve 58 and place the compressor hose (not shown) in the air intake valve 56. Inject compressed air up to a pressure of 3.5 bars, checking on the barometer 50 that said pressure has been reached. Turn off the air intake valve 56 and remove the compressor hose, then turn the compressor off.

Set a chronometer for a 3 minute moistening time of the plaster chamber 41. If said time is surpassed, it will be too damp. After said 3 minutes, turn on the air outlet valve 58 and the barometer 50 will show that the pressure has fallen to zero.

Remove the ring 94 of the fixed arm 92 and raise the lid handle 90 with the lid 16. Remove the curing container 40 from the processor 1 with the help of long pliers. Remove the plaster chamber 41 from the curing container 40 and continue with washings to eliminate wax.

For heat curing, the plaster chamber 41, either complete plaster chamber or special, with the heat curing acrylic already aggregated inside it, is permitted to rest for some minutes on a horizontal flat surface, in the open air and at ambient temperature. It is then varnished and is dried with a dryer. Cover all inlets with Paris plaster. Meanwhile, switch on the processor by turning the thermostat 72, put the protective lid 110 on the open top 10, and let the temperature rise until it is between 90° C. and 100° C. Then, remove the protective lid 1 and check the processor conditions to see if the quantity of water inside is correct, because the quantity of water decreases by evaporation due to heat. Then add any water to the processor 1 which is necessary to reach a height of 1 cm. from the upper edge 45 of the curing container 40. The curing container is placed, with water and without the plaster chamber 41, inside the processor 1 onto the table 30 with the help of suitable pliers. Then check if the water height 70 inside the processor 1 is one centimeter below the upper edge of the curing container 40. Then, after adding any necessary water to the processor 1, remove the curing container 40 from the processor.

Keep the temperature between 90° C. and 100° C. Sometimes, when water is added, the temperature can fall a little and it is necessary to replace the protective lid 110 and wait a few more minutes until the thermometer 65 shows it is at 90° C.-100° C. at which time the protective lid 110 is removed for placement of the plaster chamber 41 in the processor 1.

Place the plaster chamber 41 in the curing container 40. Add running water to cover the plaster chamber 41 up to its edge. Submerge the curing container 40 in the processor 1 with the help of long pliers and put the lid 16 on the processor 1. Then place the ring 94 of the lid handle 90 with the fixed 92 arm of the processor 1. Turn off the air outlet valve 58 and place the compressor hose on the air intake valve 56. Inject compressed air up to a pressure of 3.5 bars checking on the barometer 50 that said pressure has been reached.

Turn off the air intake valve 56 and remove the compressor hose. Turn off the compressor's air valve. Set the chronometer for a cooking time of the heat curing acrylic for about 20 to 25 minutes (25 minutes is the recommended time for dentures thicker than normal). After that period of time, turn off the thermostat 72, unplug the processor 1 and turn on the air outlet valve 58 and the pressure gage 50 will show that the pressure will fall to 0.

Remove the ring 94 from the fixed arm 92 and raise the handle 90 with the lid 16 to remove it from the processor 1. Remove the curing container 40 from the processor 1 with the help of suitable long pliers, and leave it at rest for some 10 minutes to reduce the acrylic surface tension, without removing the plaster chamber 41 from the curing container 40. Cool it with running water for 5 minutes until the water is cold and leave it again at rest for some 10 more minutes. Remove the plaster chamber 41 from the curing container 40, and remove the plaster fronts with the help of a blunt knife. Eliminate the acrylic entrances with the help of a bur, the two anterior ones and the two posterior ones. Remove plaster from the counterpart with a well-sharpened chisel, and break it in pieces upwards. Place the model with the cured denture once again in the occlusor to check if the vertical dimension has changed. Once all registers have been checked, proceed to the corresponding filing and polishing.

What is claimed is:

1. Apparatus heat curing an acrylic dental prosthesis while the prosthesis is in a plaster chamber without a dental flask comprising:
   a) a vessel for boiling or heating water, said vessel having an open top, a lid for sealing the top, an inlet for injection of compressed air into the vessel, an outlet for exhausting of compressed air, and valve means for closing and opening said inlet and said outlet,
   b) means for supplying compressed air through said inlet to said vessel,
   c) heating means for heating water held in said vessel,
   d) a curing container holding water and holding an acrylic dental prosthesis while the prosthesis is in a plaster chamber without a dental flask during heat curing of the prosthesis, said curing container having an open top, the container being removable from said pressure vessel and being capable of holding water at a level which covers said plaster chamber prior to submerging the curing container in the vessel, and
   e) a table supporting the curing container in said vessel so that the top edge of the curing container is above the level of said water held by said vessel.

2. Apparatus as claimed in claim 1 wherein said table is perforated to permit the circulation of water heated by said heating means around the curing container.

3. Apparatus as claimed in claim 2 wherein said table is foldable.

4. Apparatus as claimed in claim 2 wherein a plurality of curing containers are supported by said table.

5. Apparatus as claimed in claim 4 wherein said vessel is cylindrical.

6. Apparatus as claimed in claim 4 including a pressure gauge for measuring the pressure of said air injected into said vessel.

7. Apparatus as claimed in claim 1 wherein said heating means comprises a shielded resistance heater.

8. Apparatus as claimed in claim 7 wherein said shielded resistance heater is located within said vessel underneath said table.

9. Apparatus as claimed in claim 8 wherein the temperature of said heating means is controlled by a thermostat.

10. Apparatus as claimed in claim 9 wherein said thermostat includes a thermostat filament, and said filament is located in a pipe which extends into said vessel above said shielded resistance heater.

11. Apparatus as claimed in claim 10 wherein a thermometer for measuring the temperature of the water held in said vessel is located in a pipe which extends into said vessel.

12. Apparatus as claimed in claim 1 wherein said lid includes an external border, and a rubber ring contoured to said border, and said ring prevents the escape of compressed air from said vessel.

13. Apparatus as claimed in claim 12 wherein said lid includes a handle, said vessel includes a fixed arm, and said lid handle is fastened to said fixed arm to seal the lid to the vessel for filling of the vessel with compressed air.

14. Apparatus as claimed in claim 13 wherein said lid has a perimeter which is larger than said opening, said lid is placed inside said vessel for sealing of the vessel, and said lid handle passes over a bridge for spring-like fastening to said fixed arm.

15. Apparatus as claimed in claim 12 wherein said lid is oval shaped.

16. Apparatus as claimed in claim 12 including a safety valve for relief of excess pressure.

* * * * *

UNITED STATES PATENT AND TRADEMARK OFFICE
CERTIFICATE OF CORRECTION

PATENT NO. : 5,444,218
DATED : August 22, 1995
INVENTOR(S) : Lilian Z. Zelniker; Alberto Sternberg It is certified that error appears in the above-indentified patent and that said Letters Patent is hereby corrected as shown below:

On the title page item [76], correct the name of the first-named inventor to: Lilian Zimet de Sternberg.

Signed and Sealed this

Sixteenth Day of April, 1996

Attest:

BRUCE LEHMAN

*Attesting Officer*      *Commissioner of Patents and Trademarks*